United States Patent
Ae et al.

(10) Patent No.: US 6,495,587 B1
(45) Date of Patent: Dec. 17, 2002

(54) TRICYCLIC INDOLE-2-CARBOXYLIC ACID COMPOUND USED AS NMDA RECEPTOR ANTAGONIST

(75) Inventors: Nobuyuki Ae, Toyonaka (JP); Seiji Katayama, Nishinomiya (JP); Hisakazu Kishimoto, Ibaraki (JP); Ryu Nagata, Nishinomiya (JP)

(73) Assignee: Sumitomo Pharmaceuticals Company, Limited, Osaka-Fu (JP)

( * ) Notice: Subject to any disclaimer, the term of this patent is extended or adjusted under 35 U.S.C. 154(b) by 0 days.

(21) Appl. No.: 09/914,461

(22) PCT Filed: Mar. 17, 2000

(86) PCT No.: PCT/JP00/01694

§ 371 (c)(1),
(2), (4) Date: Aug. 29, 2001

(87) PCT Pub. No.: WO00/56711

PCT Pub. Date: Sep. 28, 2000

(30) Foreign Application Priority Data

| Mar. 23, 1999 | (JP) | ............................................. | 11-077214 |
| Dec. 9, 1999 | (JP) | ............................................. | 11-349850 |

(51) Int. Cl.[7] ........................ A61K 31/40; C07D 209/90
(52) U.S. Cl. ........................................ 514/411; 548/436
(58) Field of Search ........................... 548/436; 514/411

(56) References Cited

U.S. PATENT DOCUMENTS 5,496,843 A * 3/1996 Nagata et al. ............... 514/411

6,040,331 A * 3/2000 Yamamoto et al. ....... 514/228.2

FOREIGN PATENT DOCUMENTS

| EP | 0627434 | 12/1994 |
| EP | 0657427 | 6/1995 |
| WO | 9216205 | 10/1992 |
| WO | 9308188 | 4/1993 |
| WO | 9420465 | 9/1994 |
| WO | 9510517 | 4/1995 |
| WO | 9738691 | 10/1997 |
| WO | WO-9745410 A1 * | 12/1997 | ......... C07D/209/90 |

* cited by examiner

*Primary Examiner*—Laura L. Stockton
(74) *Attorney, Agent, or Firm*—Birch, Stewart, Kolasch & Birch, LLP

(57) ABSTRACT

The present invention provides novel tricyclic indole-2-carboxylic acids of the following chemical formula, which have potent NMDA receptor antagonistic activity.

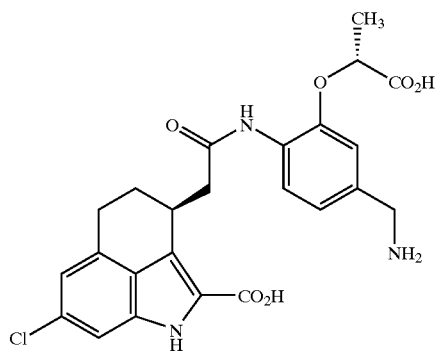

7 Claims, 2 Drawing Sheets

TRICYCLIC INDOLE-2-CARBOXYLIC ACID COMPOUND USED AS NMDA RECEPTOR ANTAGONIST

This application is the national phase under 35 U.S.C. § 371 of PCT International Application No. PCT/JP00/01694 which has an International filing date of Mar. 17, 2000, which designated the United States of America and was published in English.

TECHNICAL FIELD

The present invention relates to a tricyclic indole-2-carboxylic acid compound which is a potent N-methyl-D-aspartate (NMDA) receptor antagonist.

BACKGROUND

JP 7-188166-A (EP 657427; U.S. Pat. No. 5,496,843) discloses tricyclic indole-2-carboxylic acid derivatives useful as NMDA receptor antagonists. WO 97/38681 (EP 903144) discloses that some tricyclic nitrogen-containing compounds are useful for treating retinal neuropathy. However, those documents do not disclose specifically the tricyclic indole-2-carboxylic acid compound of the present invention.

DESCRIPTION OF THE INVENTION

The present invention is intended to provide a potent NMDA receptor antagonist. The present inventors found that the tricyclic indole-2-carboxylic acid compound of the present invention is a potent NMDA receptor antagonist and has efficient anti-convulsive activities. Thus, the present invention has been accomplished.

That is, the present invention provides a compound which is a tricyclic indole-2-carboxylic acid of formula(1):

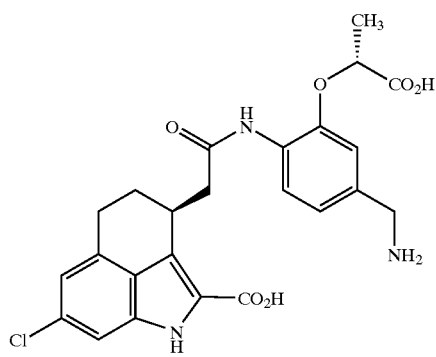

(1)

or a prodrug thereof, or a pharmaceutically acceptable salt of the said acid or prodrug, or a solvate of the said acid, prodrug or salt.

In one aspect of the invention the compound is a hydrochloride monohydrate represented by formula(2):

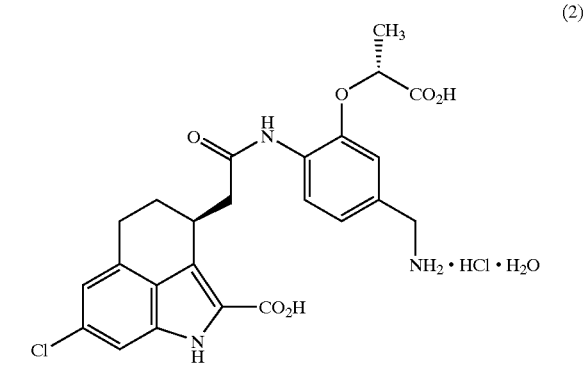

(2)

Preferably the monohydrate of formula (2) has a powder X-ray diffraction pattern having average values of diffraction angle($2\theta$) and relative intensity as given by the following table:

TABLE 1

| diffraction angle $2\theta$ (°) (average value) | relative intensity (%) (average value) |
|---|---|
| 9.9 | 100 |
| 18.8 | 66 |
| 23.0 | 69 |
| 23.3 | 60 |

The present invention further provides a compound of the invention as defined above for use in a method of treatment of the human or animal body by therapy.

The invention also provides a pharmaceutical composition comprising a compound of the invention as defined above and a pharmaceutically acceptable carrier or diluent.

In one embodiment the compound of the invention as defined above is for treating damage to the central nervous system induced by ischemic or hypoxic conditions.

In a second embodiment the compound of the invention as defined above is for treating damage to the central nervous system induced by a stroke.

In a third embodiment the compound of the invention as defined above is for treating convulsions.

The present invention further provides the use of a compound of the invention as defined above in the preparation of a medicament for treating damage to the central nervous system induced by ischemic or hypoxic conditions.

The invention also provides a method of treating damage to the central nervous system induced by ischemic or hypoxic conditions which comprises administering a compound of the invention as defined above to a patient in need thereof.

Figure 1:
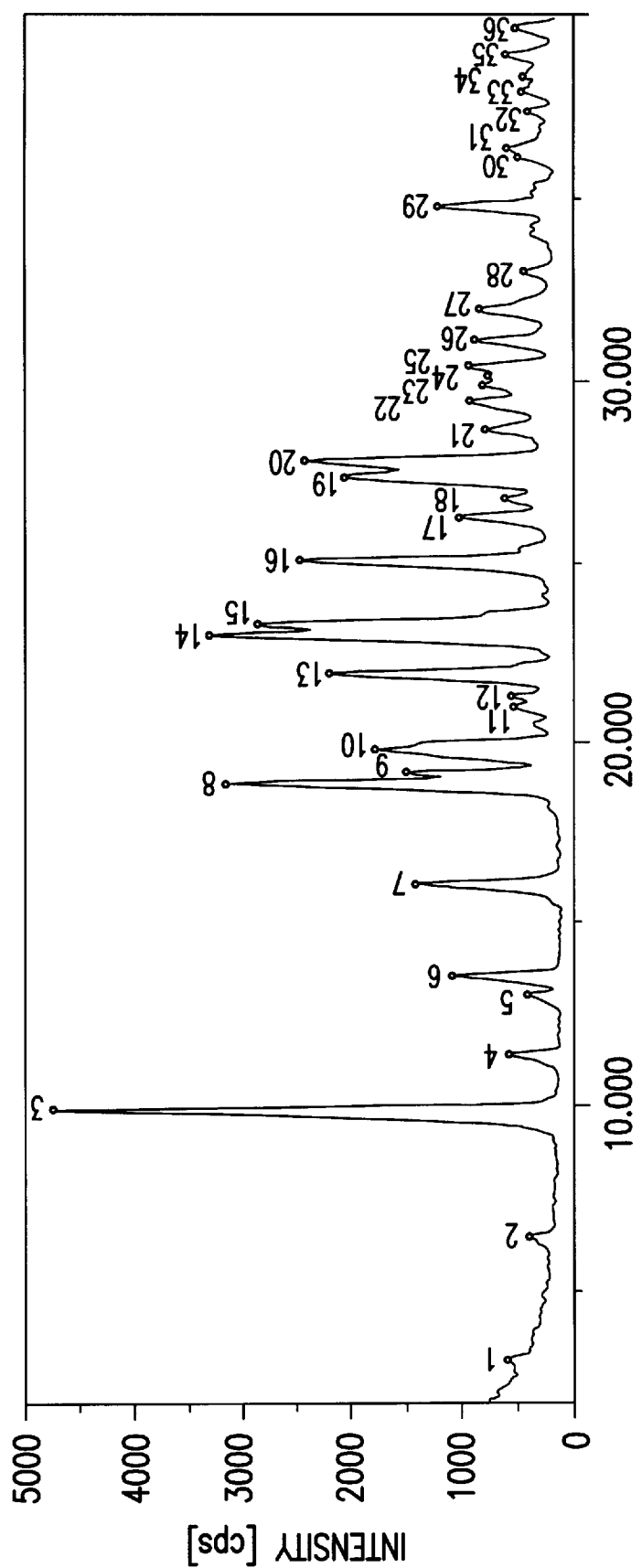
FIG. 1 shows a powder X-ray diffraction spectrum of the hydrochloride monohydrate of the tricyclic indole-2-carboxylic acid [C-5].

The prodrugs of the tricyclic indole-2-carboxylic acid of the formula (1) include prodrugs which can be hydrolyzed chemically or enzymatically in vivo to produce the parent tricyclic indole-2-carboxylic acid. Examples of the prodrug are such as those described in "Chemistry and Industry, 1980, 435" or "Advanced Drug Discovery Reviews 3, 39(1989)." Typical examples are biohydrolyzable esters of either or both of the two carboxylic groups in the tricyclic indole-2-carboxylic acid. Preferred examples of the biohydrolyzable esters include $C_1$–$C_6$ alkyl esters such as methyl ester, ethyl ester etc.; $C_3$–$C_9$ acyloxyalkyl ester such as acetoxymethyl ester, 1-acetoxyethyl ester, pivaloyloxymethyl ester etc.; $C_3$–$C_9$ alkoxycarbonyloxyallkyl esters such as isopropoxycarbonyloxymethyl ester etc.; 2-oxo-1,3-dioxol-4-yl-$C_1$–$C_6$ alkyl esters such as 2-oxo-1,3-dioxol-4-yl-methyl ester etc.; morpholinoethyl ester; and the like.

The pharmaceutically acceptable salts of the tricyclic indole-2-carboxylic acid of the formula (1) or the prodrug thereof include, for example, salts with an inorganic acid such as hydrochloride, hydrobromide, nitrate, sulfate, phosphate and the like; salts with an organic acid such as formate, acetate, trifluoroacetate, propionate, lactate, tartrate, oxalate, fumarate, maleate, citrate, malonate, mathanesulfonate and the like; salts with inorganic metal such as alkaline metal salts (lithium salt, sodium salt, potassium salt etc.), alkaline earth metal salts (magnesium salt, calcium salt, barium salt etc.), an aluminum salt and the like; salts with an organic base such as basic amino acid salts (arginine salt, lysine salt etc.), triethylammonium salt, tetrabutylammonium salt, pyridinium salt, pyrrolidinium salt, piperidinium salt and the like; or an ammonium salt. Preferred examples are salts with an inorganic acid and salts with an organic acid, preferably hydrochloride.

The solvates of the tricyclic indole-2-carboxylic acid of the formula (1) or of the prodrug or pharmaceutically acceptable salt thereof include, for example, hydrates, alcoholates such as ethanolate and the like. A preferred example is the hydrate. Especially preferred is the hydrochloride monohydrate, which is represented by the formula (2). This monohydrate has excellent moisture stability and preservation stability, which make it easy to handle the compound during production.

The tricyclic indole-2-carboxylic acid can be produced, for example, according to the method described hereunder in the Examples.

The prodrug can be produced by a conventional method. The pharmaceutically acceptable salt may be produced, for example, by mixing the compound of the formula (1) or the prodrug thereof with a pharmaceutically acceptable acid or base such as hydrochloric acid, oxalic acid, methanesulfonic acid, sodium hydroxide etc. in a solvent such as water, methanol, ethanol, acetone etc.

The solvate can be produced, for example, by heating the acid of the formula (1) or the prodrug thereof or the pharmaceutically acceptable salt of the acid or prodrug in the corresponding solvent. The hydrate can be produced, for example, by keeping the compound with a hydrophilic organic solvent containing water at 0° C. to 100° C. Suitable hydrophilic organic solvents include alcohols such as methanol, ethanol, isopropanol etc.; ketones such as acetone etc.; amides such as N,N-dimethylformamide (DMF) etc. Preferred hydrophilic solvents are alcohols, especially isopropanol. The hydrophilic organic solvent may contain 5% (v/v) to 50% (v/v) of water, more preferably 6% (v/v) to 20% (v/v) of water, especially about 9% (v/v) of water.

The compound of the present invention, a selective and potent antagonist of glycine binding site of the NMDA receptor, is useful for treating diseases caused by excessive release of glutamic acid and/or glycine from neuronal and glia cells. This is because the NMDA-glycine antagonists of the present invention regulate the function of NMDA receptors to maintain normal activity of neuronal cells and to protect them.

The diseases caused by excessive release of glutamic acid and/or glycine include, for example, damage to the central nervous system induced by ischemic or hypoxic conditions, e.g. stroke, hypoglycemia, cardiac arrest, physical trauma etc.; neurodegenerative disorders, e.g. epilepsy, Huntington's chorea, Parkinson's disease, Alzheimer's disease, dementia etc.; depression, anxiety, schizophrenia; pain; drug dependency, drug resistance, alcoholism; etc.

The compound of the present invention, having anticonvulsive activity as shown below in the Examples, is useful for treating convulsions.

The compound of the present invention can be administered not only to humans, but also to various non-human mammals such as mice, rats, dogs, cows, horses, goats, sheep, rabbits, pigs and the like.

The compound of the present invention may be administered by any convenient route, e.g. orally or parenterally, including intramuscularly, intravenously, subcutaneously, percutaneously, intranasally, rectally, intraocularly and intracerebrally. Pharmaceutical formulations for oral administration include, for example, tablets, pills, capsules, powders, granules, fine granules, suspensions, emulsions, syrups and the like. Pharmaceutical formulations for parenteral administration include, for example, injections such as solutions, emulsions, suppositories for administration through the rectum, dermal formulations, e.g. ointments, creams, lotions etc., and the like. Preferred formulations are, for example, injections for intravenous injection, intraocular formulations and dermal formulations.

These formulations can be prepared by conventional methods using conventional carriers or diluents. The solid formulations such as tablets can be reared by mixing the active compound with pharmaceutically acceptable conventional carriers or diluents such as lactose, sucrose, corn starch and the like; binders such as hydroxypropylcellulose, polyvinylpyrrolidone, hydroxypropylmethylcellulose and the like; disintegrating agents such as sodium carboxymethylcellulose, starch, sodium glycolate and the like; lubricants such as stearic acid, magnesium stearate and the like; or preservatives and the like. For parenteral formulations such as solutions and suspensions, the active compound can be dissolved or suspended in a physiologically acceptable carrier or diluent such as water, saline, oil, aqueous dextrose solution and the like, which may contain auxiliary agents such as pH adjusters, buffers, stabilizers, solubilizers, emulsifiers, salts for influencing osmotic pressure and the like, if desired.

The dose and the frequency of administration vary depending on the species to be treated, the severity of symptoms, patient's age, body weight, sex, administration route, and the like. The active compound of the present invention is usually administered to an adult (body weight of 60 kg), by the oral route in a dose of about 1 mg to about 2 g, preferably about 10 mg to about 1 g, or by parenteral route, for example, intravenously in a dose of about 0.1 mg to about 1 g, preferably about 1 mg to about 500 mg, per day in one portion or several portions or by continuous injection. The administration time may be once in 2 days to once in 1 week, wherein the administration dose can be adjusted accordingly. Intravenous injection may, for example, be performed continuously in an administration speed of about 10 mg/hr to about 200 mg/hr, preferably about 20 mg/hr to about 150 mg/hr, more preferably about 40 mg/hr to about 100 mg/hr.

EXAMPLES

The present invention is explained below precisely with examples and experiments but is, of course, not limited by them.

Process A

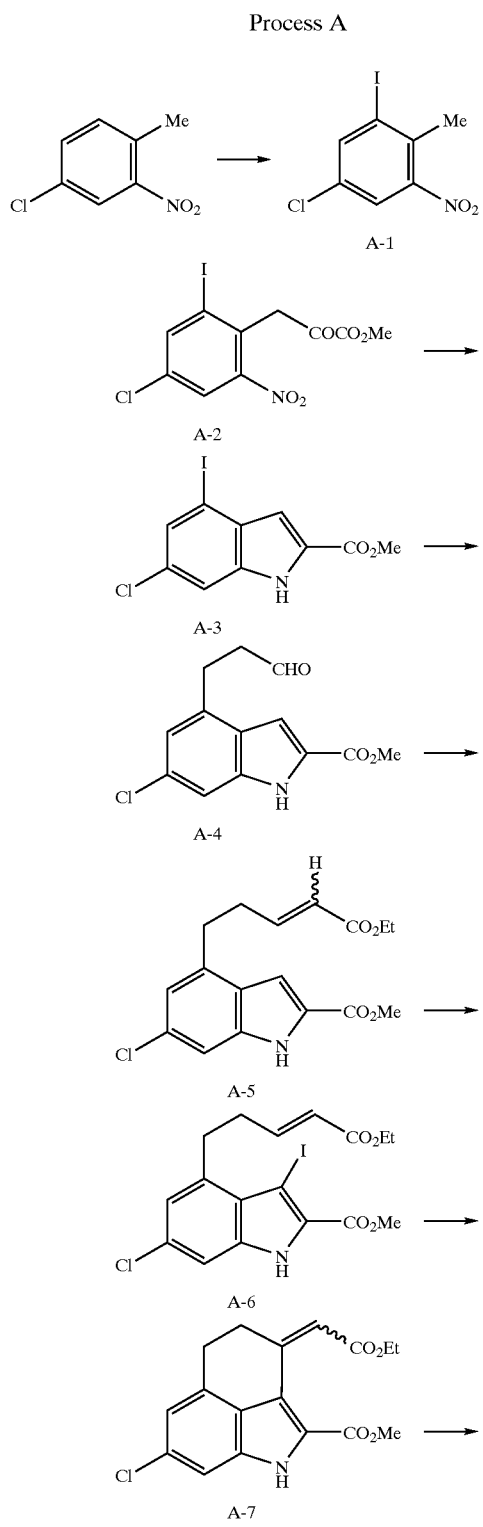

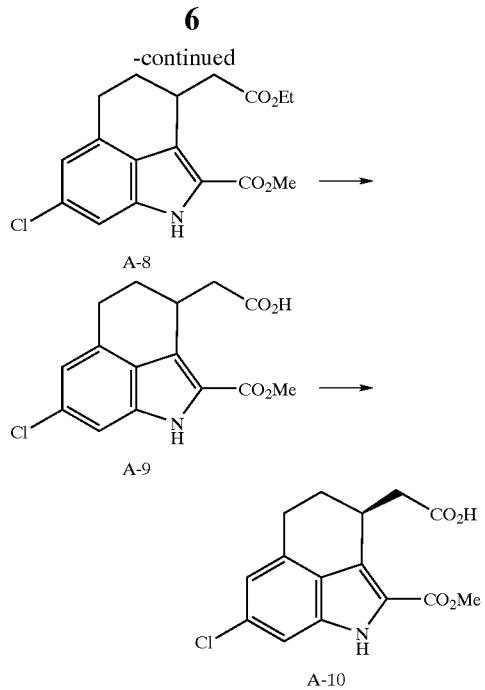

[A-1] 2-Iodo-4-chloro-6-nitrotoluene

Sodium iodate (158 g, 0.800 mol, 0.4 eq.) was added portionwise, under nitrogen atmosphere, to an ice-cooled mixture of 4-chloro-2-nitrotoluene (343 g, 2.00 mol), iodine (204 g, 0.800 mol, 0.4 eq.) and conc. sulfuric acid (1960 g, 20.0 mol, 10 eq.) and the resulting mixture was stirred at a temperature of 5° C. to 10° C. for 6 hours. Water (2 L) was added dropwise thereto with stirring in an ice-water bath, and the mixture was extracted with toluene (2.5 L). The combined organic layer was treated with aqueous 10% sodium thiosulfate solution, washed with water (1 L×2) and aqueous sat. sodium hydrogencarbonate solution (1 L×2) successively, dried over sodium sulfate and concentrated to give crude A-1 (548 g, purity 62%) as a yellow oil. This product was used in the following reaction without further purification.

$^1$H-NMR (270 MHz, CDCl$_3$) δ 2.56 (3H, s), 7.74 (1H, d, J=2.0 Hz), 8.06 (1H, d, J=2.0 Hz).

[A-2] Methyl (2-Iodo-4-chloro-6-nitrophenyl)pyruvate

Under a nitrogen atmosphere, toluene (280 mL) and dimethyl oxalate (318 g, 2.69 mol) were added to a solution of potassium methoxide (188 g, 2.69 mol) prepared in methanol (560 mL). The mixture was stirred at room temperature for 20 min and a solution of crude A-1 (200 g) obtained above in toluene (280 mL) was added dropwise thereto and the resulting mixture was stirred at room temperature for 4 hours. The reaction mixture, being occasionally diluted with methanol (about 300 mL), was poured slowly into stirred and ice-cooled 5N hydrochloric acid (600 mL). Ethyl acetate (1 L) and water (600 mL) were added. The organic layer was separated and the aqueous layer was extracted with a mixture of ethyl acetate (200 mL) and toluene (100 mL). The organic layers were combined and concentrated, and toluene (500 mL) was added to the residue and evaporated again to give crude A-2 (374 g) as a brown oil. This product was used to produce A-3 without further purification.

$^1$H-NMR (270 MHz, CDCl$_3$) δ 3.95 (3H, s), 4.70 (2H, s), 8.01 (1H, d, J=2.0 Hz), 8.15 (1H, d, J=2.0 Hz).

[A-2] Methyl (2-Iodo-4-chloro-6-nitrophenyl)pyruvate (Alternative Method)

Under a nitrogen atmosphere, dimethyl oxalate (199 g, 1.68 mol) was added to a 28% methanolic sodium methoxide solution (324 g, 1.68 mol). The mixture was stirred at room temperature for 30 min and a solution of crude A-1 (100 g) obtained above in toluene (340 mL) was added dropwise thereto at room temperature. After stirring for 16 hours at room temperature, the reaction mixture, being occasionally diluted with methanol (100 to 200 mL), was poured slowly into stirred and ice-cooled 5N hydrochloric acid (300 mL). Water (600 mL) and a mixture of ethyl acetate (500 mL) and toluene (250 mL) were added, and the organic layer was separated and the aqueous layer was extracted with a mixture of ethyl acetate (100 mL) and toluene (50 mL). The organic layers were combined and concentrated, and toluene (300 mL) was added to the residue and concentrated again to give crude A-2 (165 g) as a brown oil. This product was used in the following reaction without further purification.

[A-3] Methyl 4-Iodo-6-chloroindole-2-carboxylate

Under a nitrogen atmosphere, a solution of crude A-2 (220 g) obtained above in dimethoxyethane (410 mL) was added dropwise to a solution of $SnCl_2.2H_2O$ (299 g, 1.33 mol) in dimethoxyethane (410 mL) at room temperature and the mixture was stirred for 1 hour. After aqueous 20% $TiCl_3$ solution (682 g, 0.884 mol) was added dropwise under cooling in an ice-water bath, the mixture was stirred for a further hour. 6N Hydrochloric acid (1.4 L) and a mixture of ethyl acetate (1.6 L) and toluene (0.8 L) were added. The resulting mixture was warmed to room temperature and the organic layer was separated, washed with 1N hydrochloric acid (1.4 L) and concentrated to give crude A-3 (158 g).

A suspension of the crude A-3 thus obtained in acetonitrile (1.55 L) was stirred and heated under reflux for 30 min and then stirred at about 30° C. for 1 hour. The precipitates produced were collected by filtration, washed with ice-cooled acetonitrile (150 mL, 60 mL×2) and dried under reduced pressure to give A-3 (75.9 g, 53% from 4-chloro-2-nitrotoluene) as a white solid.

$^1$H-NMR (270 MHz, DMSO-$d_6$) δ 3.89 (3H, s), 6.91 (1H, s), 7.48 (1H, m), 7.56 (1H, d, J=2.0 Hz), 12.5 (1H, br.s).

[A-4] Methyl 4-(2-Formylethyl)-6-chloroindole-2-carboxylate

To a solution of A-3 (87.5 g, 261 mmol) in DMF (440 mL) under a nitrogen atmosphere were added sodium hydrogencarbonate (43.9 g, 522 mmol, 2.0 eq.), benzyltriethylammonium chloride (59.5 g, 261 mmol, 1.0 eq.), palladium diacetate (1.17 g, 5.22 mmol, 0.02 eq.) and allyl alcohol (30.3 g, 522 mmol, 2.0 eq.). The mixture was stirred at a temperature of 40° C. to 50° C. for 2 hours and then allowed to cool to room temperature. A solution of sodium thiosulphate pentahydrate (2.6 g, 10.4 mmol) in water (18 mL) was added and the resulting mixture was stirred vigorously at room temperature for 20 min. Activated charcoal (4.4 g) was added and stirred for 15 min. The mixture was filtered and the solid collected on the filter was washed with DMF (60 mL). Water (1.5 L) was added slowly dropwise to the combined filtrate with stirring in an ice-bath and then stirred at room temperature for 30 min. The precipitates were collected by filtration, washed with water (300 mL×2) and dried under reduced pressure to give A-4 (62.5 g, 90%) as a white solid.

$^1$H-NMR (270 MHz, CDCl$_3$) δ 2.90 (2H, t, J=7.4 Hz), 3.20 (2H, t, J=7.4 Hz), 3.96 (3H, s), 6.96 (1H, d, J=1.7 Hz), 7.22 (1H, d, J=1.7 Hz), 7.29 (1H, d, J=1.3 Hz), 9.06 (1H, br.s), 9.86 (1H, t, J=1.0 Hz).

[A-5] Methyl 4-(4-Ethoxycarbonyl-3-butenyl)-6-chloroindole-2-carboxylate

To a suspension of potassium t-butoxide (39.9 g, 356 mmol, 1.1 eq.) in tetrahydrofuran (THF; 516 mL) under a nitrogen atmosphere was added dropwise slowly triethyl phosphonoacetate (79.8 g, 356 mmol, 1.1 eq.) at room temperature and the mixture was stirred for 30 min. A solution of A-4 (86.0 g, 324 mmol) in THF (860 mL) was added dropwise at room temperature followed by stirring for 1.5 hours. Water (1.2 L) was added thereto and extracted with a mixture of ethyl acetate (0.9 L) and toluene (0.9 L). The organic layer was washed with water (1.2 L×2) and concentrated to give crude A-5 (111 g) as a white solid. This product was used in the following reaction without further purification.

$^1$H-NMR (270 MHz, CDCl$_3$) δ 1.29 (3H, t, J=7.2 Hz), 2.63 (2H, m), 3.02 (2H, m), 3.96 (3H, s), 4.19 (2H, q, J=7.2 Hz), 5.87 (1H, d, J=15.8 Hz), 6.95 (1H, d, J=1.65 Hz), 7.02 (1H, dt, J=15.8, 6.9 Hz), 7.21 (1H, t, J=1.0 Hz), 7.29 (1H, s), 9.02 (1H, br.s).

[A-6] Methyl 3-Iodo-4-(4-ethoxycarbonyl-3-butenyl)-6-chloroindole-2-carboxylate

To stirred DMF (400 mL) under nitrogen atmosphere, was added portionwise sodium iodide (53.6 g, 357 mmol) under cooling in a water-bath and then a solution of N-chlorosuccinimide (47.7 g, 357 mmol) in DMF (400 mL) was added slowly and the mixture was stirred at room temperature for 1 hour. A solution of crude A-5 (100 g) obtained above in DMF (400 mL) was added slowly followed by stirring at room temperature for 2 hours. To the reaction mixture were added dropwise aqueous 10% sodium thiosulphate solution (600 mL) and water (2.2 L) and the resulting mixture was stirred at room temperature for 2 hours. Precipitates produced were collected by filtration, washed with water (500 mL×3) and dried under reduced pressure to give A-6 (128 g 95% from A-4) as a white solid.

$^1$H-NMR (270 MHz, CDCl$_3$) δ 1.31 (3H, t, J=7.2 Hz), 2.61 (2H, m), 3.44 (2H, m), 3.99 (3H, s), 4.21 (2H, q, J=7.2 Hz), 5.94 (1H, d, J=15.8 Hz), 6.94 (1H, d, J=1.7 Hz), 7.10 (1H, dt, J=15.8, 6.9 Hz), 7.32 (1H, d, J=1.7 Hz), 9.35 (1H, br.s).

[A-7] Methyl 7-Chloro-3-ethoxycarbonylmethylidene-1,3,4,5-tetrahydrobenz[c.d]indole-2-carboxylate To a solution of A-6 (6.00 g, 13.0 mmol) and tetrakis(triphenylphosphine)palladium(0) (300 mg, 0.26 mmol. 0.02 eq.) in DMF (60 mL) under a nitrogen atmosphere were added silver phosphate (4.35 g, 10.4 mmol) and water (12 mL) at room temperature, and the mixture was stirred at about 90° C. for 3.5 hours and then allowed to cool. The reaction mixture was treated with activated charcoal (300 mg) at room temperature for 15 min and filtered. The collected solid on the filter was washed with a mixture of ethyl acetate (25 mL) and toluene (25 mL). To the combined filtrate and washings were added water (50 mL) and a mixture of ethyl acetate (25 mL) and toluene (25 mL). The organic layer was separated, washed with water (30 mL×2), treated with activated charcoal (300 mg) and magnesium sulphate and was concentrated under reduced pressure to give crude A-7 (4.67 g) as a brown solid. This product was used in the following reaction without further purification.

$^1$H-NMR (270 MHz, CDCl$_3$) δ 1.34 (3H, t, J=7.2 Hz), 3.06 (1H, t, J=6.5 Hz), 3.48 (1H, t, J=6.5 Hz), 3.99 (1H, s), 4.24 (1H, q, J=7.2 Hz), 6.96 (1H, d, J=1.3 Hz), 7.21 (1H, d, J=1.3 Hz), 7.26 (1H, s), 8.99 (1H, br.s).

[A-8] Methyl 7-Chloro-3-ethoxycarbonylmethyl-1,3,4,5-tetrahydrobenz[c.d]indole-2-carboxylate To a solution of A-6 (45.0 g, 97.5 mmol) in monochlorobenzene (1.8 L), being heated under reflux under a nitrogen atmosphere, were added dropwise a solution of tributyltin hydride (34.0 g, 117 mmol, 1.2 eq.) and azobisisobutyronitrile (4.00 g, 24.4 mmol, 0.25 eq.) in monochlorobenzene (200 mL), and the mixture was heated under reflux for a further hour. The reaction mixture was allowed to cool to room temperature and the solvent was evaporated under reduced pressure. Acetonitrile (300 mL), hexane (300 mL) and activated charcoal (4.5 g) were added to the residue and the mixture was stirred vigorously at room temperature for 30 min and filtered. The acetonitrile layer was separated and the hexane layer was extracted with acetonitrile (100 mL). The combined acetonitrile layer was washed with hexane (300 mL×3) and concentrated under reduced pressure to give crude A-8 (31.3 g). This product was used in the following reaction without further purification.

[A-8] Methyl 7-Chloro-3-ethoxycarbonylmethyl-1,3,4,5-tetrahydrobenz[c.d]indole-2-carboxylate To a mixture of crude A-7 (1.72 g) obtained above, THF (12 mL), methanol (0.640 mL, 15.8 mmol) and samarium (1.58 g, 10.5 mmol) under a nitrogen atmosphere was added slowly a solution of iodine (1.21 g 4.78 mmol) in THF (5 mL) at a temperature of 0° C. to 3° C. and stirred for 2 hours. Triethylamine (1.33 mL, 9.56 mmol) was added and the mixture was warmed to room temperature and stirred for 3 hours. After 1N hydrochloric acid (30 mL) was added slowly maintaining the temperature between 0° C. to 5° C., ethyl acetate (30 mL) was added and the resulting mixture was stirred vigorously at room temperature for 15 min. The organic layer was separated, washed with 1N hydrochloric acid (15 mL×2), aqueous 10% sodium thiosulfate solution (15 mL×2) and brine (10 mL) successively, treated with activated charcoal (85 mg) and magnesium sulfate (260 mg) at room temperature for 10 min, filtered and concentrated under reduced pressure to give crude A-8 (1.67 g). This product was used in the following reaction without further purification.

$^1$H-NMR (270 MHz, CDCl$_3$) δ 1.28 (3H, t, J=7.3 Hz), 2.01 (1H, m), 2.17 (1H, m), 2.48 (1H, dd, J=14.9, 10.5 Hz), 2.73 (1H, dd, J=14.9, 4.0 Hz), 2.82 (1H, m), 3.00 (1H, m), 3.92 (1H, m), 3.95 (3H, s), 4.18 (2H, q, J=7.3 Hz), 6.88 (1H, s), 7.17 (1H, s), 8.70 (1H, br.s).

[A-9] Methyl 7-Chloro-3-carboxymethyl-1,3,4,5-tetrahydrobenz[c.d]indole-2-carboxylate Under a nitrogen atmosphere, crude A-8 (113 g) obtained above was dissolved in acetic acid (620 mL) at 80° C. Conc. hydrochloric acid (245 mL) was added and the mixture was stirred at 80° C. for 3.5 hours and then cooled to room temperature. Water (1250 mL) was added and the mixture was extracted with a mixture of THF (1225 mL) and ethyl acetate (3675 mL). The organic layer was washed with water (1250 mL×2), treated with activated charcoal (6.5 g) at room temperature for 10 min, filtered and concentrated under reduced pressure to give crude A-9 (111.3 g). A mixture of the crude A-9 (111.3 g) and acetonitrile (490 mL) was stirred under reflux for 1 hour and allowed to cool to room temperature. The precipitated crystals were collected by filtration, washed with acetonitrile (60 mL×3) and dried under reduced pressure to give A-9 (57.8 g, 56% from A-6) as white crystals.

$^1$H-NMR (270 MHz, DMSO-d$_6$) δ 1.88 (1H, m), 2.11 (1H, br.d, J=12.5 Hz), 2.37 (1H, dd, J=15.2, 10.6 Hz), 2.56 (1H, dd, J=15.2, 4.3 Hz), 2.80 (1H, br.d, J=17.2 Hz), 2.94 (1H, br.t, J=13.9 Hz), 3.77 (1H, m), 3.88 (3H, s), 6.84 (1H, s), 7.17 (1H, s), 11.60 (1H, s), 12.17 (1H, br.s).

[A-10] Methyl (3S)-7-Chloro-3-carboxymethyl-1,3,4,5-tetrahydrobenz[c.d]indole-2-carboxylate Under a nitrogen atmosphere, A-9 (21.0 g, 68.2 mmol) was dissolved in isopropanol (1050 mL) under reflux. A solution of L-(−)-norephedrine (10.3 g, 68.2 mmol) in isopropanol (210 mL) was added dropwise and the mixture was stirred under reflux for 10 min, cooled gradually and then stirred at room temperature. The precipitated crystals were collected by filtration, washed with ice-cooled isopropanol (50 mL×2) and dried under reduced pressure to give the crude L-(−)-norephedrine salt of A-10 (14.8 g, 79.7% ee).

Under a nitrogen atmosphere, a mixture of the crude L-(−)-norephedrine salt of A-10 (29.4 g, 78.6% ee) and isopropanol (590 mL) was stirred and heated under reflux for 4 hours, and then cooled gradually to room temperature. The precipitated crystals were collected by filtration, washed with ice-cooled isopropanol (60 mL×2) and dried under reduced pressure to give the L-(−)-norephedrine salt of A-10 (25.1 g, 98.5% ee).

The L-(−)-norephedrine salt of A-10 (64.2 g) was dissolved in a mixture of 1N hydrochloric acid (500 mL), ethyl acetate (1.5 L) and THF (0.5 L). The organic layer was separated, washed with water (500 mL×2), treated with activated charcoal (3.0 g) and magnesium sulfate, and filtered. The filtrate was concentrated under reduced pressure, and the solid residue was suspended in acetonitrile, filtered, washed with acetonitrile and dried under reduced pressure to give A-10 (41.9 g, 98.1% ee).

$^1$H-NMR (270 MHz, DMSO-d$_6$) δ 1.88 (1H, m), 2.11 (1H, br.d, J=12.5 Hz), 2.37 (1H, dd, J=15.2, 10.6 Hz), 2.56 (1H, dd, J=15.2, 4.3 Hz), 2.80 (1H, br.d, J=17.2 Hz), 2.94 (1H, br.t, J=13.9 Hz), 3.77 (1H, m), 3.88 (3H, s), 6.84 (1H, s), 7.17 (1H, s), 11.60 (1H, s), 12.17 (1H, br.s).

Process B

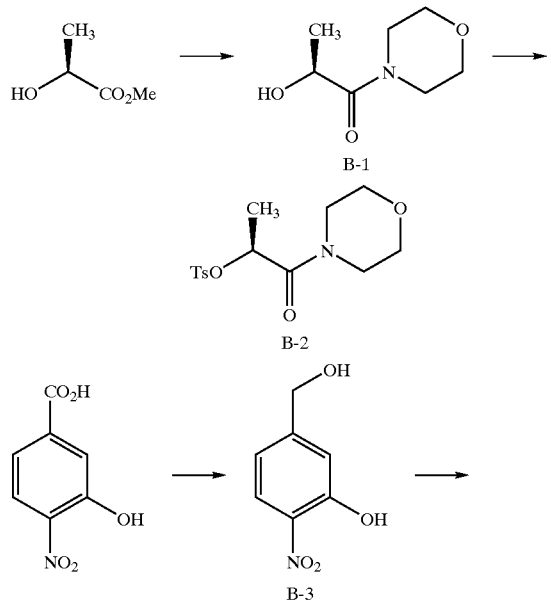

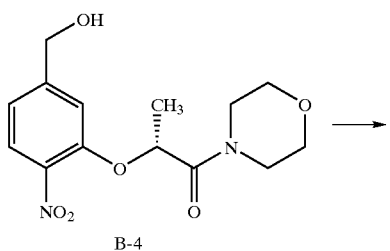
B-4

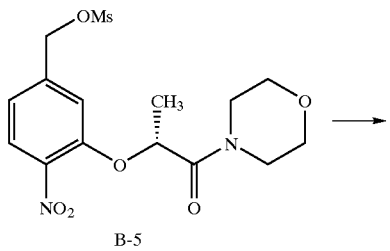
B-5

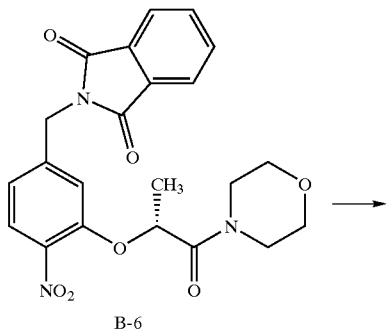
B-6

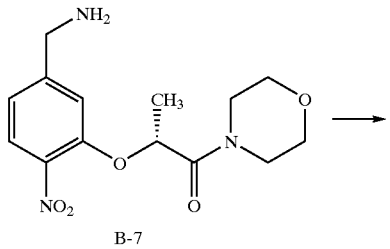
B-7

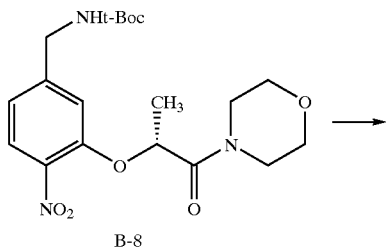
B-8

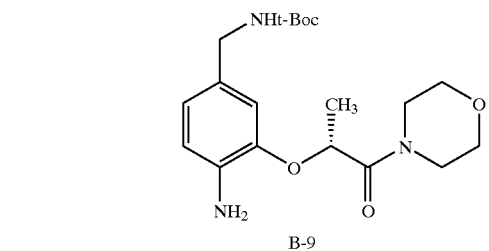
B-9

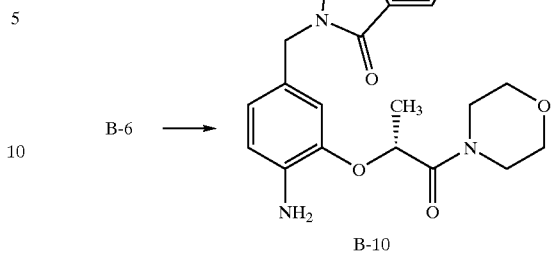
B-10

[B-1] N-((2S)-2-Hydroxypropanoyl)morpholine

Under a nitrogen atmosphere, 60% sodium hydride (1.92 g, 0.048 mol) was added slowly portionwise to a mixture of methyl L-lactate (50.0 g, 0.48 mol) and morpholine (46 mL, 0.528 mol) with stirring in an ice-bath, and the resulting mixture was stirred at 50° C. for 3 hours. Toluene was added thereto and evaporated under reduced pressure. This procedure was repeated further twice to give B-1.

[B-2] N-((2S)-2-p-Toluensulfonyloxypropanoyl) morpholine

Under a nitrogen atmosphere, to a suspension of 60% sodium hydride (20.2 g, 0.504 mol) in THF (400 mL) was added dropwise a solution of B-1 obtained above in THF (400 mL) with stirring in an ice-bath, and the mixture was warmed gradually and stirred at 5° C. for 30 min. After the mixture was cooled in an ice-bath, a solution of p-toluenesulfonyl chloride (110 g, 0.576 mol) in THF (400 mL) was added dropwise followed by stirring for 2 hours. The reaction mixture was acidified with 1N hydrochloric acid to pH 1 and extracted with ethyl acetate (ca. 500 mL). Combined extracts were washed with water and brine successively, dried over sodium sulfate and concentrated under reduced pressure. To the residue were added diethyl ether (ca. 100 mL) and hexane (ca. 30 mL). The precipitated crystals were collected by filtration, washed with diethyl ether and dried to give B-2 (110 g, 73% from methyl L-lactate).

$^1$H-NMR (270 MHz, CDCl$_3$) δ 7.81 (d, 2H, J=8.3 Hz), 7.35 (d, 2H, J=8.3 Hz), 5.27 (q, 1H, J=6.6 Hz), 3.63 (m, 4H), 3.57 (m, 3H), 3.42 (m, 1H), 2.46 (s, 3H), 1.47 (d, 3H, J=6.6 Hz).

[B-3] 5-Hydroxymethyl-2-nitrophenol

To a solution of 3-hydroxy-4-nitrobenzoic acid (50.0 g, 0.273 mol) in dichloroethane (1000 mL) under a nitrogen atmosphere were added trimethoxyborane (45.4 g, 0.437 mol) and boron trifluoride diethyl etherate (62.0 g, 0.437 mol) followed by dropwise addition of borane-pyridine complex (38.1 g, 0.410 mol). After stirring at room temperature for 4 hours, methanol (100 mL) was added dropwise under cooling in an ice-bath. The mixture was concentrated under reduced pressure and toluene (400 mL) was added to the residue. The resulting mixture was extracted with aqueous 1N NaOH solution (300 mL×3), and the combined aqueous layers were acidified with conc. hydrochloric acid to pH 1 and extracted with ethyl acetate (500 mL and 300 mL). The organic layers were combined, washed with water (300 mL×2) and brine successively aid dried over magnesium sulfate, and the solvent was evaporated under reduced pressure to give B-3 (43.3 g, 94%).

¹H-NMR (270 MHz, CDCl₃) δ 10.65 (s, 1H), 8.09 (d, 1H, J=8.6 Hz), 7.17 (d, 1H, J=1.7 Hz), 6.96 (dd, 1H, J=8.6, 1.7 Hz), 4.77 (s, 2H), 1.94 (br.s, 1H).

[B-4] 2-((1R)-1-Morpholinocarbonylethoxy)-4-hydroxymethylnitrobenzene

Under a nitrogen atmosphere, potassium carbonate (52.7 g, 0.381 mol) was added to a solution of B-3 (43.0 g, 0.254 mol) and B-2 (83.6 g, 0.267 mol) in DMF (150 mL) and the mixture was stirred at 50° C. for 6 hours. Water (ca. 400 mL) was added thereto and the resulting mixture was extracted with dichloromethane (300 mL×2). The organic layers were combined and washed with aqueous 5% potassium carbonate solution, 1N hydrochloric acid and water successively, dried over magnesium sulfate, and the solvent was evaporated under reduced pressure to give crude B-4 (93.2 g, 99% ee).

¹H-NMR (270 MHz, CDCl₃) δ 7.80 (d, 1H, J=8.3 Hz), 7.11 (d, 1H, J=1.6 Hz), 7.02 (dd, 1H, J=8.3, 1.6 Hz), 5.09 (q, 1H, J=6.9 Hz), 4.72 (d, 2H, J=5.6 Hz), 4.15 (t, 1H, J=5.6 Hz), 3.87 (m, 1H), 3.68 (m, 4H), 3.51 (m, 3H), 1.67 (d, 3H, J=6.9 Hz).

[B-5] 2-((1R)-1-Morpholinocarbonylethoxy)-4-methanesulfonyloxymethylnitrobenzene Under a nitrogen atmosphere, methanesulfonyl chloride (36.1 g, 0.315 mol) was added dropwise slowly to a solution of crude B-4 (93.0 g) and triethylamine (50.1 mL, 0.360 mol) in dichloromethane (500 mL), with stirring in an ice-bath. 1N Hydrochloric acid (ca. 300 mL) was added and the organic layer was separated, washed with water, dried over magnesium sulfate, and the solvent was evaporated under reduced pressure to give B-5 (97.0 g, 99% from B-3).

¹H-NMR (270 MHz, CDCl₃) δ 7.85 (d, 1H, J=8.2 Hz), 7.11 (d, 1H, J=1.7 Hz), 7.09 (dd, 1H, J=8.2, 1.7 Hz), 5.24 (s, 2H), 5.08 (q, 1H, J=6.9 Hz), 3.92 (m, 1H), 3.69 (m, 4H), 3.48 (m, 3H), 3.09 (s, 3H), 1.70 (d, 3H, J=6.9 Hz).

[B-6] 2-((1R)-1-Morpholinocarbonylethoxy)-4-phthalimidomethylnitrobenzene

Under a nitrogen atmosphere, potassium phthalimide (50.8 g, 0.274 mol) was added to a solution of B-5 (96.7 g, 0.249 mol) in DMF (800 mL). The mixture was stirred at room temperature for 1.5 hours and, after addition of water (1000 mL), extracted twice with 700 mL of ethyl acetate/toluene(2:1 v/v). The organic layers were combined, washed with water (400 mL×3) and brine successively and dried over magnesium sulfate, and the solvent was evaporated to give a residue (108 g). To the residue thus obtained were added diethyl ether (ca. 400 mL) and toluene (ca. 50 mL) The precipitated crystals were collected by filtration, washed with diethyl ether and dried under reduced pressure to give B-6 (73.6 g, 67%).

¹H-NMR (270 MHz, CDCl₃) δ 7.87 (m, 2H), 7.80 (d, 1H, J=7.3 Hz), 7.75 (m, 2H), 7.10 (d, 1H, J=1.7 Hz), 7.08 (dd, 1H, J=7.3, 1.7 Hz), 5.02 (q, 1H, J=6.9 Hz), 4.88 (d, 1H, J=15.2 Hz), 4.81 (d, 1H, J=15.2 Hz), 3.88 (m, 1H), 3.71–3.51 (m, 4H), 3.49–3.31 (m, 3H), 1.65 (d, 3H, J=6.9 Hz).

[B-7] 2-((1R)-1-Morpholinocarbonylethoxy)-4-aminomethylnitrobenzene

To a solution of B-6 (73.4 g, 0.167 mol) in THF (800 mL) under a nitrogen atmosphere were added hydrazine monohydrate (32.4 mL, 0.668 mol) and p-toluenesulfonic acid monohydrate (3.18 g, 0.0167 mol). The mixture was stirred and heated under reflux for about 6 hours and then cooled to room temperature, basified with aqueous 5% potassium carbonate solution (1000 mL) to pH 10, and extracted with dichloromethane (500 mL×2, 200 mL). The organic layers were combined, washed with water (1 L), dried over magnesium sulfate, and the solvent was evaporated under reduced pressure to give B-7 (47.3 g, 92%).

¹H-NMR (270 MHz, CDCl₃) δ 7.83 (d, 1H, J=8.3 Hz), 7.13 (s, 1H), 7.05 (d, 1H, J=8.3 Hz), 5.09 (q, 1H, J=6.9 Hz), 3.96 (m, 1H), 3.93 (s, 2H), 3.69 (m, 4H), 3.56–3.38 (m, 3H), 1.69 (d, 3H, J=6.9 Hz), 1.50 (br.s, 2H).

[B-8] 2-((1R)-1-Morpholinocarbonylethoxy)-4-t-butoxycarbonylaminomethylnitrobenzene Di-t-butyl dicarbonate (36.6 g, 0.167 mol) was added to a solution of B-7 (47.1 g, 0.152 mol) in ethyl acetate (800 mL) under a nitrogen atmosphere, and the mixture was stirred at room temperature for about 1 hour. After the solvent was evaporated under reduced pressure, the residue was dissolved in toluene (ca. 400 mL) with heating and the solution thus obtained was stirred at room temperature and then in an ice-bath for 2 hours. The precipitated (crystals were collected by filtration, washed with toluene and dried at 50° C. under reduced pressure to give B-8 (58.1 g, 93%, 99.7% ee).

¹H-NMR (270 MHz, CDCl₃) δ 7.82 (d, 1H, J=8.6 Hz), 7.00 (m, 2H), 5.07 (m, 1H), 5.06 (q, 1H, J=6.9 Hz), 4.32 (d, 2H, J=6.4 Hz), 3.91 (m, 1H), 3.69 (m, 4H), 3.55–3.37 (m, 3H), 1.68 (d, 3H, J=6.9 Hz), 1.46 (s, 9H).

[B-9] 2-((1R)-1-Morpholinocarbonylethoxy)-4-t-butoxycarbonylaminomethylaniline

A mixture of B-8 (20.0 g, 48.9 mmol), ethyl acetate (500 mL) and palladium on activated carbon (5.0 g, Pd 10%: dry weight basis, wet: water 50%) was stirred at room temperature under a hydrogen atmosphere for 3 hours. The reaction mixture was dried over magnesium sulfate and filtered on a Celite™ under a nitrogen atmosphere, and the solvent was evaporated under reduced pressure to give B-9 (19.4 g, quantitative yield).

¹H-NMR (270 MHz, CDCl₃) δ 6.73 (d, 1H, J=7.6 Hz), 6.70 (s, 1H), 6.66 (d, 1H, J=7.6 Hz), 4.98 (q, 1H, J=6.6 Hz), 4.80 (br.s, 1H), 4.14 (d, 2H, J=7.3 Hz), 3.89 (br.s, 2H), 3.63–3.52 (m, 8H), 1.60 (d, 3H, J=6.6 Hz), 1.45 (s, 9H).

[B-10] 2-((1R)-1-Morpholinocarbonylethoxy)-4-phthalimidomethylaniline

A mixture of B-6 (11.0 g, 25 mmol), DMF (77 mL) and palladium on activated carbon (2.0 g, Pd 10%: dry weight basis, wet: water 50%) was stirred at 40° C. under a hydrogen atmosphere for 3.5 hours. The reaction mixture was filtered on a Celite™ bed and the solid on the bed was washed with DMF (10 mL×2). The combined filtrate was diluted with water (75 mL) and cooled to room temperature. The precipitated crystals were collected by filtration, washed with water (10 mL×2) and THF (10 mL×2) successively and dried under reduced pressure to give B-10 (8.71 g, 85%).

¹H-NMR (270 MHz, CDCl₃) δ 7.71–7.78 (m, 2H), 7.59–7.65 (m, 2H), 6.85 (dd, 1H, J=1.8, 7.9 Hz), 6.79 (d, 1H, J=1.8 Hz), 6.57 (d, 1H, J=7.9 Hz), 4.95 (q, 1H, J=6.7 Hz), 4.62 (s, 2H), 3.83 (bs, 2H), 3.41–3.68 (m, 8H), 1.52 (d, 3H, J=6.7 Hz).

Process C

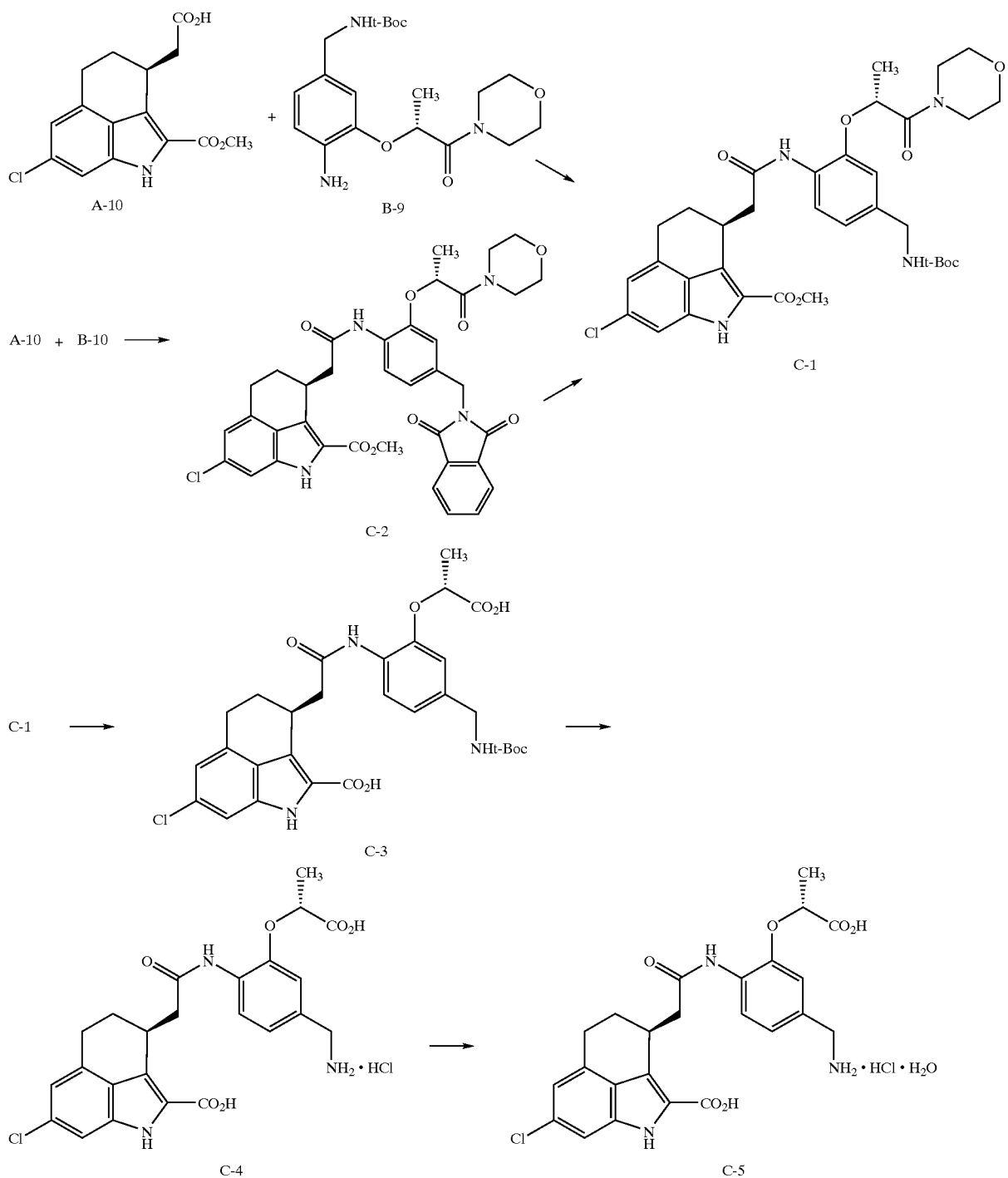

[C-1] Methyl (3S)-7-Chloro-3-(2-((1R)-1-morpholinocarbonylethoxy)-4-t-butoxycarbonylaminomethylphenyl)aminocarbonylmethyl-1,3,4,5-tetrahydrobenz[c.d]indole-2-carboxylate Oxalyl chloride (16.9 g, 133 mmol) was added dropwise slowly, under a nitrogen atmosphere, to a mixture of A-10 (39.0 g, 127 mmol), ethyl acetate (390 mL) and DMF (0.196 mL) with stirring, in an ice-bath and the mixture was stirred at room temperature for 2 hours. The solvent and the excess oxalyl chloride were evaporated and the residue was dissolved in ethyl acetate (260 mL) to give a solution of the acid chloride of A-10 in ethyl acetate.

To a solution of B-9 (57.7 g, 152 mmol) in ethyl acetate (ca. 880 mL) was added triethylamine (26.5 mL, 190 mmol) followed by dropwise addition of the solution obtained above of the acid chloride of A-10 in ethyl acetate with stirring in an ice-bath. The reaction mixture was stirred in an ice-bath for 1 hour and at room temperature for a further hour. The reaction mixture was acidified with aqueous 5% potassium hydrogensulfate solution (500 mL) to pH 2 and extracted with ethyl acetate (800 mL). The extract was washed with water (500 mL), aqueous sat. sodium hydrogencarbonate solution (400 mL), water (500 mL) and brine (200 mL) successively, dried over magnesium sulfate and the solvent was evaporated under reduced pressure to give crude C-1 (88.5 g).

The crude C-1 thus obtained was dissolved in toluene (450 mL) with heating, and the solution was cooled gradually and stirred at room temperature. The precipitated crystals were collected by filtration, washed with toluene (80 mL×2) and dried under reduced pressure at 40° C. to give C-1 (83.0 g, 98%).

$^1$H-NMR (270 MHz, CDCl$_3$) δ 9.02 (s, 1H), 8.82 (s, 1H), 8.36 (d, 1H, J=8.3 Hz), 7.18 (s, 1H), 6.93 (d, 1H, J=8.3 Hz), 6.86 (m, 1H), 4.95 (q, 1H, J=6.6 Hz), 4.88 (m, 1H), 4.23 (m, 2H), 4.03 (m, 1H), 3.83 (s, 3H), 3.59 (m, 6H), 3.43 (m, 2H), 3.12 (m, 1H), 2.84 (m, 2H), 2.59 (dd, 1H, J=14.0, 10.1 Hz), 2.29 (m, 1H), 2.04 (m, 1H), 1.57 (d, 3H, J=6.6 Hz), 1.46 (s, 9H).

[C-2] Methyl (3S)-7-Chloro-3-(2-((1R)-1-morpholinocarbonylethoxy)-4-pthalimidomethylphenyl)aminocarbonylmethyl-1,3,4,5-tetrahydrobenz[c.d]indole-2-carboxylate To a solution cooled at −13° C. of ethyl chloroformate (1.20 mL, 12.6 mmol) in THF (6 mL) was added dropwise a solution of A-10 (3.69 g, 12.0 mmol) and triethylamine (1.86 mL, 13.3 mmol) in THF (9 mL) and the mixture was stirred for 30 min at the same temperature. A solution of B-10 (5.40 g, 13.2 mmol) in DMF (65 mL) was added dropwise thereto followed by stirring at 0° C. to 5° C. for 1 hour and then at room temperature overnight. The reaction mixture was, after addition of water (45 mL) and brine (5 mL), extracted with ethyl acetate (60 mL, 35 mL). The extracts were combined, washed with aqueous 2.5% potassium hydrogensulfate solution (30 mL), brine (15 mL), aqueous saturated sodium hydrogencarbonate solution (15 mL) and brine (15 mL) successively, dried over sodium sulfate, and concentrated under reduced pressure. The crystalline residue was washed with hexane with stirring, collected by filtration and dried under reduced pressure to give C-2 (8.03 g, 96%).

$^1$H-NMR (300 MHz, CDCl$_3$) δ 8.81 (s, 1H), 8.62 (s, 1H), 8.28 (d, 1H, J=8.4 Hz), 7.70–7.80 (m, 2H), 7.60–7.70 (m, 2H), 7.19 (s, 1H), 7.18 (d, 1H, J=8.4 Hz), 6.94 (d, 1H, J=11.8 Hz), 6.79 (bs, 1H), 4.93 (q, 1H, J=6.6 Hz), 4.64 (d, 1H, J=14.5 Hz), 4.62 (d, 1H, J=14.5 Hz), 3.80–3.99 (m, 1H), 3.78 (s, 3H), 3.35–3.60 (m, 8H), 2.95–3.08 (m, 1H), 2.68–2.78 (m, 2H), 2.49 (dd, 1H, J=14.1, 10.1 Hz), 2.15–2.25 (m, 1H), 1.88–2.02 (m, 1H), 1.49 (d, 3H, J=6.6 Hz).

[C-1] Methyl (3S)-7-Chloro-3-(2-((1R)-1-morpholinocarbonylethoxy)-4-t-butoxycarbonylaminomethylphenyl)aminocarbonylmethyl-1,3,4,5-tetrahydrobenz[c.d]indole-2-carboxylate Hydrazine monohydrate (0.56 mL, 11.5 mmol) was added to a mixture of C-2 (1.60 g, 2.29 mmol), THF (4 mL) and methanol (8 mL) and the resulting mixture was stirred at 50° C. for 5 hours. The reaction mixture was, after addition of water (6 mL) and aqueous sat. sodium hydrogencarbonate solution (5 mL), extracted with ethyl acetate (20 mL, 10 mL). The extracts were combined and washed with aqueous sat. sodium hydrogencarbonate solution and brine successively and dried over sodium sulfate, and the solvent was evaporated to give the residue (1.365 g). To a solution of the residue (678 mg) in ethyl acetate (7 mL) was added a solution of di-t-butyl dicarbonate (286 mg, 1.31 mmol) in ethyl acetate (0.5 mL) and the resulting mixture was stirred at room temperature for 1 hour. The solvent was evaporated and the residue was crystallized by triturating with toluene (4 mL). The crystals were collected by filtration to give C-1 (740 mg, 97%).

[C-3] (3S)-7-Chloro-3-(2-((1R)-1-carboxyethoxy)-4-t-butoxycarbonylaminomethylphenyl)aminocarbonylmethyl-1,3,4,5-tetrahydrobenz[c.d]indole-2-carboxylic Acid Under a nitrogen atmosphere, to a mixture of C-1 (86.4 g 129 mmol). THF (440 mL) and methanol (440 mL) was added aqueous 2N lithium hydroxide solution (440 mL. 880 mmol) and stirring was continued at room temperature for 16 hours. The organic solvent was evaporated under reduced pressure and the resulting aqueous layer was washed with toluene (300 mL×3), acidified with a solution of potassium hydrogensulfate (145 g) in water (1 L) to pH 2 and extracted with a mixture of ethyl acetate and THF (3:1 v/v: 1000 mL, 500 mL×2). The organic layers were combined, washed with water (700 mL) and brine (300 mL) successively and, after addition of activated charcoal (4.0 g) and magnesium sulfate (1.0 g), stirred and filtered. The solvent was evaporated to give crude C-3 (73.1 g).

A mixture of the crude C-3 (72.0 g) and acetonitrile (360 mL) was heated under reflux, cooled gradually and stirred at room temperature for 1 hour. The crystals formed were collected by filtration, washed with ice-cooled acetonitrile (30 mL×3) and dried under reduced pressure to give C-3 (70.3 g, 94%).

$^1$H-NMR (270 MHz, CDCl$_3$) δ 12.99 (br.s, 2H), 11.42 (s, 1H), 9.07 (s, 1H), 7.89 (d, 1H, J=8.3 Hz), 7.31 (m, 1H), 7.15 (s, 1H), 6.84 (m, 3H), 4.75 (q, 1H, J=6.6 Hz), 4.04 (m, 2H), 3.87 (m, 1H), 3.10 (m, 1H), 2.81–2.62 (m, 3S), 2.13 (m, 1H), 1.85 (m, 1H), 1.56 (d, 3H, J=6.6 Hz), 1.40 (s, 9H).

[C-4] (3S)-7-Chloro-3-(2-((1R)-1-carboxyethoxy)-4-aminomethylphenyl)aminocarbonylmethyl-1,3,4,5-tetrahydrobenz[c.d]indole-2-carboxylic Acid Hydrochloride Under a nitrogen atmosphere, to a solution of C-3 (70.0 g, 119 mmol) in acetic acid (280 mL) seas added 1N hydrogen chloride in acetic acid (240 mL, 240 mmol) at room temperature and the mixture was stirred at the same temperature for 2 hours. Toluene (1040 mL) was added thereto and stirred for 30 min. The precipitated solid was collected by filtration, washed with toluene (50 mL×3) and dried under reduced pressure to give C-4 (61.2 g, 99%).

$^1$H-NMR (270 MHz, DMSO-d$_6$) δ12.83 (br.s, 2H), 11.42 (s, 1H), 9.16 (s, 1H), 8.39 (br.s, 3H), 8.05 (d, 1H, J=8.2 Hz), 7.21 (d, 1H, J=1.7 Hz), 7.15 (s, 1H), 7.07 (dd, 1H, J=8.2, 1.7 Hz), 6.82 (s, 1H), 4.84 (q, 1H. J=6.9 Hz), 3.93 (m, 3H), 3.10 (m, 1H), 2.81–2.59 (m, 3H), 2.09 (m, 1H), 1.86 (m, 1H), 1.58 (d, 3H, J=6.9 Hz).

[C-5] (3S)-7-Chloro-3-(2-((1R))-1-carboxyethoxy)-4-aminomethylphenyl)aminocarbonylmethyl-1,3,4,5-tetrahydrobenz[c.d]indole-2-carboxylic Acid Hydrochloride Monohydrate A mixture of C-4 (400 mg, 0.766 mmol), isopropanol (4 mL) and water (0.4 mL) was stirred and heated at 80° C. for 1 hour, and then cooled to room temperature and stirred for a further 30 min. The crystals formed were collected by filtration to give C-5 (261 mg, 63%).

Melting point: 232–237° C. (decomp.); Elemental analysis (C$_{24}$H$_{27}$Cl$_2$N$_3$O$_7$); Calculated (%): C, 53.34, H, 5.04, Cl, 13.12, N, 7.78. Found (%) C, 53.25 H, 4.97, Cl, 13.10, N 7.66.

Reference Example
Preparation of the Epimer

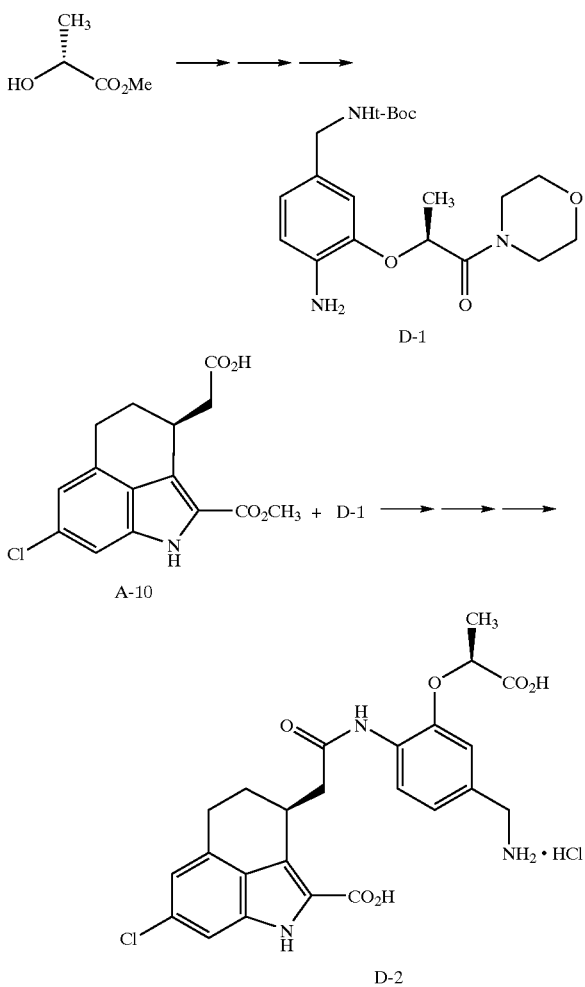

[D-1] 2-((1S)-1-Morpholinocarbonylethoxy)-4-butoxycarbonylaminomethylaniline

The title compound was prepared from methyl D-lactate by the procedure similar to that described above in the production of [B-1] to [B-9]. The NMR spectrum of the title compound was the same as in [B-9].

[D-2] (3S)-7-Chloro-3-(2-((1S)-1-carboxyethoxy)-4-aminomethylphenyl)aminocarbonylmethyl-1,3,4,5-tetrahydrobenz[c.d]indole-2-carboxylic Acid Hydrochloride The title compound was prepared from [A-10] and [D-1] by the procedure similar to that described above in the production of [C-1] to [C-4].

$^1$H-NMR (270 MHz, DMSO-$d_6$) δ 13.0 (br.s, 2H), 11.44 (s, 1H), 9.29 (s, 1H), 8.20 (br.s, 3H), 8.01 (d, 1H, J=8.2 Hz), 7.16 (m, 2H), 7.06 (d, 1H, J=8.2 Hz), 6.85 (s, 1H), 4.81 (q, 1H, J=6.9 Hz), 3.95 (s, 2H), 3.87 (m, 1H), 1.80–3.30 (m, 6H), 1.59 (d, 3H, J=6.9 Hz).

Experiment 1
Powder X-ray Diffraction Spectrum of the Hydrochloride Monohydrate Powder X-ray diffraction spectra were measured using 1.541 Å of Cu.Kα with the X-ray diffraction spectrometer RINT 2500V (Rikagaku Electric Co. Ltd.).

The average values of diffraction angles (2θ) and relative intensities in the powder X-ray diffraction spectrum of the hydrochloride monohydrate [C-5] are given above in Table 1. The powder X-ray diffraction spectrum is shown in FIG. 1.

The average values of the diffraction angle has normal precision, for example, about ±0.1. The relative intensity also has normal precision.

Experiment 2
Preservation Stability of the Hydrochloride Monohydrate

The hydrochloride monohydrate [C-5] was kept at a temperature of 60° C., in a sealed tube or under 75% R.H.(relative humidity) for 4 weeks. Thereafter, the remaining amount of the compound was assayed with high performance liquid chromatography (HPLC). The results are shown in Table 2.

TABLE 2

Stability at 60° C. of the hydrochloride monohydrate [C-5]

| Duration of preservation | HPLC integrated intensity (%) | |
| --- | --- | --- |
| | in a sealed tube | under 75% R.H. |
| Initial | 99.3 | 99.3 |
| 2 weeks | 99.3 | 99.2 |
| 4 weeks | 99.6 | 99.5 |

HPLC charts did not show any increase of impurities or degradation products, and no characteristic changes of the compound were observed.

Experiment 3
Characteristic Moisture Absorption

Characteristic moisture absorption of the crystalline hydrochloride monohydrate [C-5] and the hydrochloride [C-4] which is in the form of an amorphous powder were measured with a Vapor Sorption Analyzer MB300G-3 (VTI Corporation).

Figure 2:
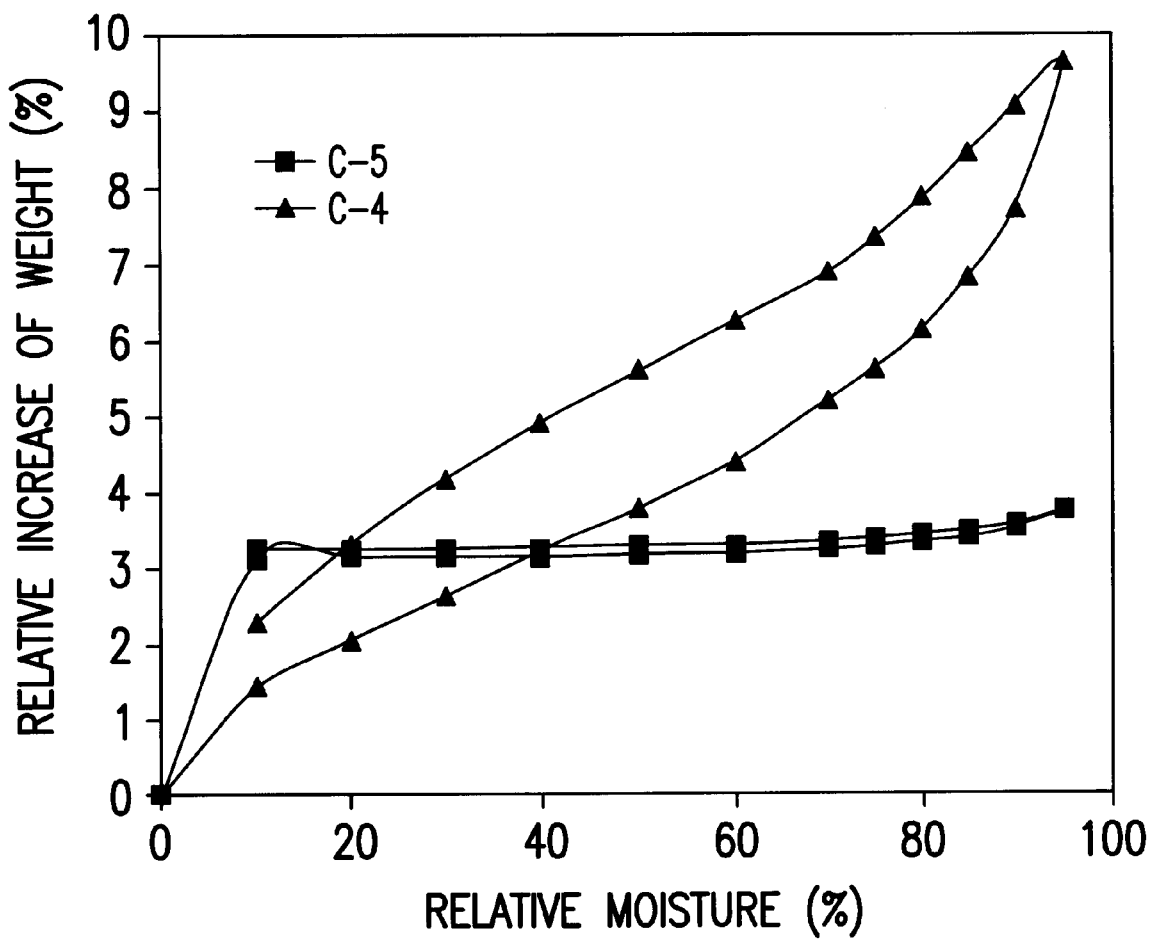
FIG. 2 shows a chart indicating the characteristic moisture absorption property of the hydrochloride monohydrate [C-5] and the amorphous powder of the hydrochloride [C-4].

In advance of measurement, the weighed samples put in the Analyzer were dehydrated at 60° C. under reduced pressure. The change in weight of the samples was measured, while moisture in the Analyzer was, at a temperature of 25° C., continuously increased from 0% R.H. to 95% R.H. and then decreased from 95% R.H. to 10% R.H. The change in weight of the sample compared to the weight of the dehydrated sample, as the relative humidity varies, is shown in FIG. 2.

The dehydrated crystalline compound [C-5] rapidly took up one molecular equivalent of water, theoretically 3.45 wt %, in a moist atmosphere, and thereafter the weight was almost unchanged during the experiment. On the other hand, the amorphous compound [C-4-] freely absorbed water, i.e. more than 2.5 molecular equivalents of water, in accordance with the increase of moisture.

Experiment 4
Anti-convulsion Test

Twenty minutes after intravenous administration of the test compound (1 to 10 mg/kg) into each of ten mice tested, NMDA (5 nmol) was administered intracerebroventricularly (i.c.v.). Under the conditions without pretreatment of the test compound, mice exhibit tonic convulsions. The number of mice which did not exhibit tonic convulsions after i.c.v. administration of NMDA was counted as an index of anti-convulsive efficacy. The hydrochloride [C-4] at 10 mg/kg i.v. protected 90% of mice from tonic convulsions. This compound showed efficient dose-dependency, and $ED_{50}$ was 2.3 mg/kg.

Experiment 5

[³H]-DCKA Binding Test

A crude rat brain synaptic membrane preparation was washed three time with 50 mM Tris acetate buffer (pH 7.4) and centrifuged at 50,000×g for 30 min. The pellets obtained were suspended in 0.32M sucrose solution and stored at −80° C. For binding studies, the frozen suspension was thawed, treated with 0.08–0.10% triton X-100 at 2° C. for 10 min. The membrane suspension was washed twice and centrifuged at 50,000×g for 30 min. The synaptic membrane thus prepared (ca. 100 μg of protein) was incubated with 10 nM [³H]-5,7-dichlorokynurenic acid (DCKA) and the test compound (10 to 0.1 ng/mL) at 2° C. for 10 min in 50 mM Tris acetate buffer (pH 7.4). The incubation was terminated by suction filtration using Whatman GF/B glass filter. The radioactivity bound to the membrane on the filter was measured by scintillation counting. Non-specific binding was calculated by the radioactivity measured under the incubations in the presence of 0.1 mM glycine. The hydrochloride [C-4] and its epimer [D-2] inhibited [³H]-DCKA binding with the $IC_{50}$ values of 1.4 nM and 16 nM, respectively.

Industrial Applicability

The present invention provides a potent NMDA receptor antagonist.

What is claimed is:

1. A tricyclic indole-2-carboxylic acid of formula:

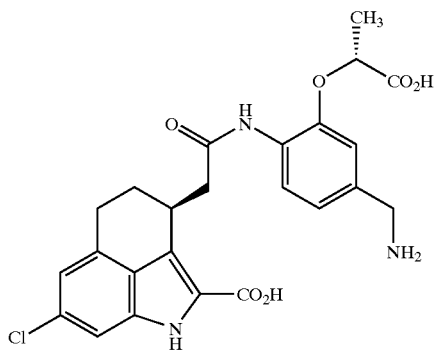

or a prodrug thereof or a pharmaceutically acceptable salt of the said acid or prodrug, or a solvate of the said acid, prodrug or salt.

2. A compound according to claim 1, which is a hydrochloride monohydrate represented by formula:

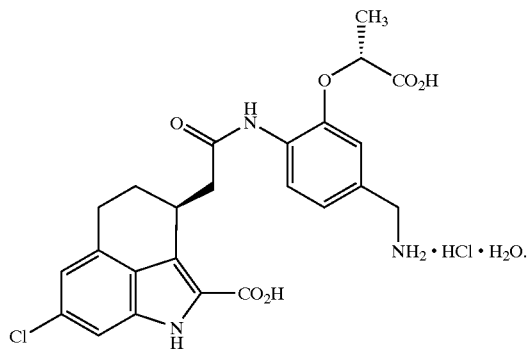

3. A compound according to claim 2 having a powder X-ray diffraction pattern having average values of diffraction angle (2θ) and relative intensity as given in the following table:

| diffraction angle 2θ (°) (average value) | relative intensity (%) (average value) |
|---|---|
| 9.9 | 100 |
| 18.8 | 66 |
| 23.0 | 69 |
| 23.3 | 60 |

4. A pharmaceutical composition comprising a compound as defined in claim 1, 2 or 3 and a pharmaceutically acceptable carrier or diluent.

5. A method of treating a damage to the central nervous system induced by an ischemic or hypoxic condition which comprises administering a compound as defined in claim 1, 2 or 3 to a patient in need thereof.

6. A method of treating damage to the central nervous system induced by a stroke which comprises administering a compound as defined in claim 1, 2 or 3 to a patient in need thereof.

7. A method of treating convulsion which comprises administering a compound as defined in claim 1, 2 or 3 to a patient in need thereof.

* * * * *